United States Patent [19]

Leight

[11] Patent Number: 5,727,566
[45] Date of Patent: Mar. 17, 1998

[54] TRACKABLE EARPLUG

[75] Inventor: Howard S. Leight, San Diego, Calif.

[73] Assignee: Howard S. Leight and Associates, Inc., San Diego, Calif.

[21] Appl. No.: 770,407

[22] Filed: Dec. 20, 1996

Related U.S. Application Data

[60] Provisional application No. 60/010,461, Jan. 23, 1996.

[51] Int. Cl.$^6$ ..................... A61F 11/00
[52] U.S. Cl. .................. 128/857; 128/864
[58] Field of Search ................. 128/846, 857, 128/864–868; 2/2; 181/130, 135

[56] References Cited

U.S. PATENT DOCUMENTS

| | | | |
|---|---|---|---|
| 1,355,276 | 10/1920 | Schutz | 128/864 |
| 2,446,707 | 8/1948 | Leight | 128/864 |
| 2,573,923 | 4/1951 | Mezz . | |
| 2,619,960 | 12/1952 | Reynolds . | |
| 2,876,767 | 3/1959 | Wasserman | 128/865 |
| 3,110,356 | 11/1963 | Mendelson . | |
| 4,219,018 | 8/1980 | Draper, Jr. . | |
| 4,349,082 | 9/1982 | Gastmeier . | |
| 4,916,758 | 4/1990 | Jordan-Ross | 128/866 |
| 4,936,411 | 6/1990 | Leonard . | |
| 5,405,402 | 4/1995 | Dye . | |

FOREIGN PATENT DOCUMENTS

| | | |
|---|---|---|
| 0 244 979 | 11/1987 | European Pat. Off. . |
| 22 173 110 A | 8/1986 | United Kingdom . |
| WO 90/07306 | 12/1990 | WIPO . |

*Primary Examiner*—Michael A. Brown
*Attorney, Agent, or Firm*—Freilich Hornbaker Rosen

[57] ABSTRACT

An earplug is described, which includes an elastic earplug body (12) and a metal part (14) mounted to the body to form an earplug that can be detected by a metal detector. The metal part (14) is in the form of a band that is clamped around the body. Where the body includes a narrow stem (24) and at least one flange (34) extending from a position (56) on the body and at a radially outward and rearward incline therefrom, the band can be attached to a location (62) lying a small distance rearward of the position where the flange emerges from the stem, so the band is hidden and is prevented from directly engaging a person's ear canal.

10 Claims, 1 Drawing Sheet

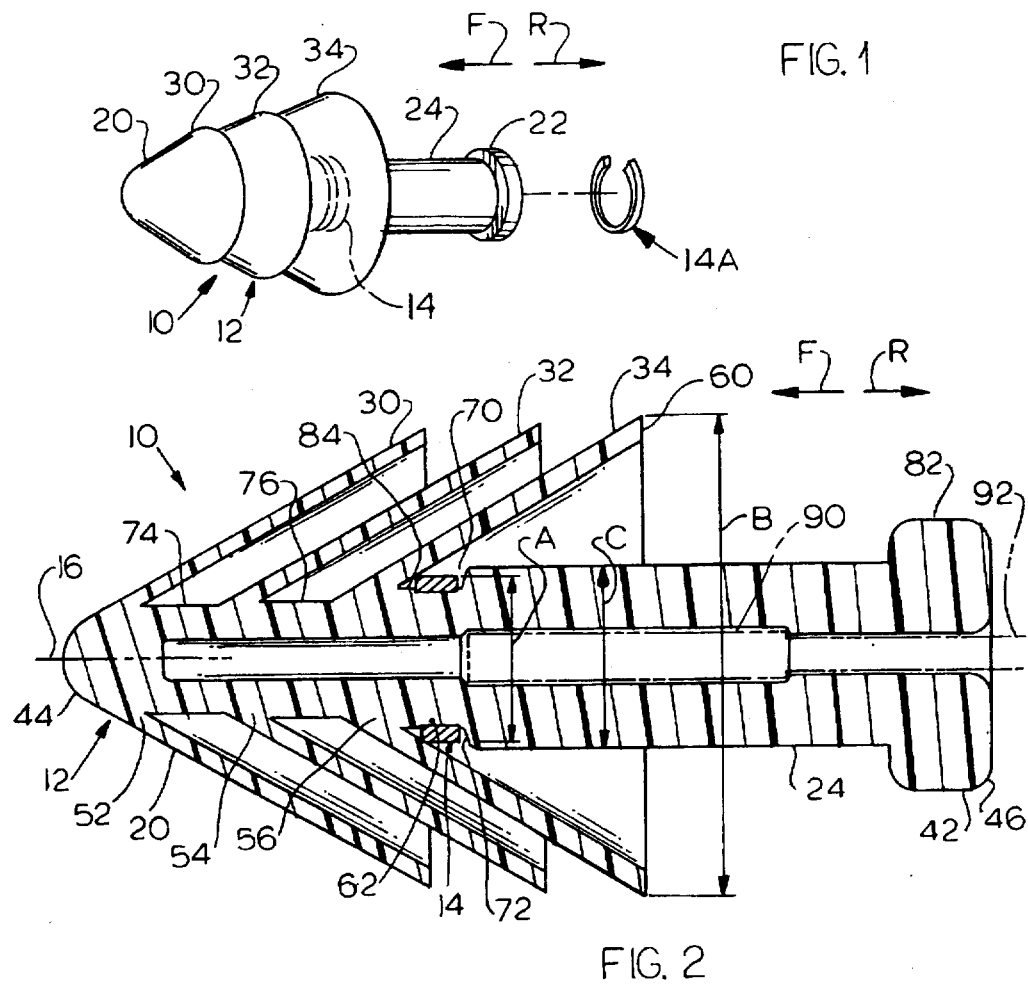
FIG. 1
FIG. 2
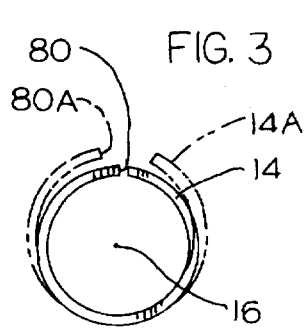
FIG. 3
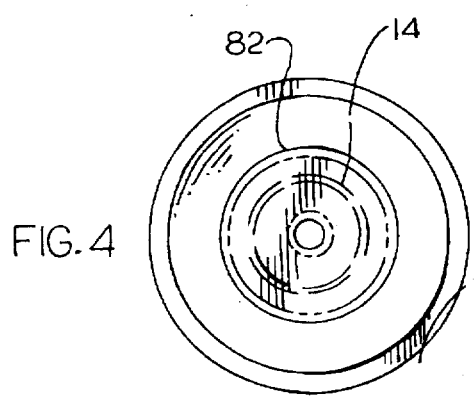
FIG. 4

5,727,566

TRACKABLE EARPLUG

CROSS-REFERENCE TO RELATED CASE

This application claims the benefit of U.S. Provisional Application number 60/010,461 filed Jan. 23, 1996.

BACKGROUND OF THE INVENTION

Earplugs are worn by industrial workers to protect their hearing. However, when worn by workers in the food or pharmaceutical industry, there is danger of product contamination if an earplug should fall into the material being processed. Such industries use detectors for metallic and other objects, but such detectors usually cannot detect earplugs molded of foam plastic or other plastic or rubber. European patent publication 244,979 and U.S. Pat. No. 4,936,411 show a metal object inserted into a deep hole or channel extending along the axis of a solid rubber or other polymer earplug. It can require substantial cost to insert the object and securely lock it in place. A detectable part which could be easily attached to an earplug body in a low cost manner, would be of value.

SUMMARY OF THE INVENTION

In accordance with one embodiment of the present invention, a detectable earplug is provided, which can be constructed at low cost. The earplug includes a molded earplug body having an axis extending in forward and rearward directions and having a forward portion that first enters a person's ear canal. The earplug includes a detectable part attached to the body. The detectable part comprises a band which extends around the body and about the body axis, and which is clamped to a location on the body.

The earplug body may be of the type that includes a stem and one or more flanges that extend from a position along the stem and in a generally radially outward and rearward incline therefrom. The band can lie immediately rearward of the position from which the flange extends from the stem. This results in the band being isolated from the person's ear canal by the flange, and in the band being relatively hidden from view.

The novel features of the invention are set forth with particularity in the appended claims. The invention will be best understood from the following description when read in conjunction with the accompanying drawings.

BRIEF DESCRIPTION OF THE DRAWINGS

FIG. 1 is an exploded isometric view showing an earplug and a band that can be mounted on the earplug.

FIG. 2 is a sectional view showing the earplug of FIG. 1 with the band fully installed thereon.

FIG. 3 is an axial view of just the band of FIG. 1, showing the band in its final installed configuration, and also showing, in phantom lines, the band in its initial configuration prior to installation on the earplug body.

FIG. 4 is a rear elevation view of the earplug of FIG. 2.

DETAILED DESCRIPTION OF THE INVENTION

FIG. 1 illustrates an earplug 10 of the present invention, which includes an earplug body 12 and a detectable part 14A that can be mounted on the body. The body is molded of an elastomeric polymer such as a foam or non-foam plastic or rubber. While engineering plastics have a modulus of elasticity of over 100,000 psi, elastomeric material has a modulus of elasticity of less than 50,000 psi. The body has an axis 16 extending in forward and rearward directions F, R. A forward portion 20 of the body is constructed to enter the ear canal of a person and block noise, the body having a rearward portion 22 that usually projects out of the ear canal and that can be grasped to pull out the earplug from the ear canal. The particular earplug shown includes a largely cylindrical stem 24 extending along the axis, and three cone-shaped flanges 30, 32, 34 extending from the stem. The detectable part is in the form of a metal (e.g. steel) band that can be clamped around the stem as indicated at 14, to secure the band on the earplug body 12. The metal band allows the earplug to be detected by X-ray detectors, metal detectors, magnetic detectors, and other scanning apparatus.

FIG. 2 shows the band 14 fully attached to the earplug body 12. The stem 24 is considered to extend along the entire length of the body, between its front and rear ends 40, 42. Each of the flanges 30, 32, 34 is joined to the stem at a position 52, 54, 56 at the front portion of the stem, and extends generally in a radially outward (with respect to axis 16) and rearward (R) direction, or incline from the corresponding position 52–56. Each flange has a rearward end, with the rearward end of the rearmost flange 34 indicated at 60.

Applicant prefers to mount the band 14 around the stem 24, at an axial location 62 that lies between the position 56 where the flange is joined to the stem, and the rear end 60 of the flange, with the band preferably mounted immediately rearward of the front end of the flange. This has the advantage that the band 14 is largely hidden from view. While the earplug body 12 is molded and generally of attractive shape, the band 14 may be of a different color and may not be chrome plated for enhanced appearance. The mounting of the flange at location 62 largely hides it so it does not detract from the appearance of the entire earplug. The largely hidden band helps avoid workers "playing" with the band, and possibly loosening it. In addition, the location of the band helps assure that the band will not touch the ear canal of a person. When the band is inserted in the ear canal, the flange 34 lies around the band so it cannot touch the ear canal. When the earplug is withdrawn from the ear canal, the flanges such as 34 may curl around. However, because the band 14 is close to the forward end of the flange at 56, the curled-around flange still protects the ear against contact with the band. Although burrs are removed from the band, contact of the band with the ear canal still may hurt the ear canal, and therefore is highly undesirable.

Applicant forms a groove or recess 70 in the stem, with the band 14 lying in the recess and slightly compressing the elastomeric material of the stem. The recess has a rearward wall 72 that extends primarily perpendicular to the cylindrical surface of much of the stem and the stem has a greater diameter immediately rearward of the recess, which helps to avoid the possibility of the band 14 sliding rearwardly along the stem and coming off, even if the stem should be expanded by a workman. It would be possible to mount the band at stem locations 74, 76 that lie between the forward and rearward ends of the other flanges, although it is somewhat easier to install the band at the location of the recess 70.

The band 14 is initially formed in the configuration 14A shown in FIG. 3, of a detectable material such as steel. The band at 14A has a gap 80A of about 30° with respect to the axis 16 of the earplug and of the band. To attach the band, the rearmost flange 34 (FIG. 2) is folded partially forward and pulled forwardly, while the rear of the earplug which has a knob 82 formed thereon, is pulled rearwardly. This tension in the stem results in reduction in diameter of the stem at the bottom 84 of the groove. With the stem under tension, the portion of the stem at the groove can fit through the gap 80 in the band, to be surrounded by the band at 14A. Thereafter, the band at 14A is squeezed closed to the configuration shown at 14, wherein the width of the band at 14A has been greatly reduced. The reduction in gap width substantially eliminates the possibility that the band will fall off the earplug during use, while also resulting in the band slightly biting into the earplug groove bottom wall to prevent movement of the band with respect to rest of the earplug. The original size of the gap 80 is preferably more than 15°, with the particular gap shown being 30° (about the axis 16). When the band is clamped on the earplug, with the gap being reduced to that shown at 80, the gap width is preferably less than 15°, with a particular gap 80 being about 3°. It is possible to mount the narrow bands in the groove.

The provision of a detectable band or other detectable attachment lying around the outside of a location on the earplug, results in several advantages. One advantage is that the band can be easily applied to the earplug with low cost equipment. Holes do not have to be pierced into the earplug body, and adhesive does not have to be applied to hold the band in the body. The secure mounting of the band and its resistance to removal, can be easily ascertained because the band is readily available and visible (especially when the rearmost flange 34 is turned forward). A batch of earplugs can be easily checked to be sure they are of the type that has a detectable attachment, by merely bending over the rearmost flange 34 to view the presence of the band. The use of a detectable band with the earplug stem lying therewithin, is especially useful for an earplug of the type that has a plurality of thin flanges and a small diameter stem. This is because the band is mounted on the stem and does not affect use of the earplug; that is, the band does not affect the noise blocking ability, or the ease of insertion or withdrawal of the earplug body from the ear canal.

Other shapes of detectable attachments can be used by mounting them around the outside of the earplug, any of such attachments herein referred to as a band. The ear canal of people, within about one inch of the outside of the canal, generally ranges between 0.28 and 0.38 inch. Applicant prefers that the outside diameter of the band 14 (after band attachment) be less than 0.28 inch and preferably less than 0.24 inch, so the band does not rigidly limit the outer diameter of the flange 34 when the flange is completely bent inward and compressed. It is noted that applicant prefers to use flanges such as 34 having a thickness of about 0.035 inch, but the material of the flanges is easily compressed. The outside diameter of the rear end 60 of the flange 34 is preferably more than 0.38 inch, to block noise through ear canals of a range of sizes. In an earplug that applicant has designed, the earplug stem has a diameter C of 0.23 inch, the band has an outside diameter A of 0.20 inch, and the rearmost flange has an undeflected outside diameter B of 0.50 inch. The earplug has an overall length of 1.17 inch.

The particular earplug shown is a type that is designed to receive a ferrule 90 at the end of a cord 92 that connects two earplugs together. However, the band 14 does not affect whether or not the cord is used. Where a cord is used, it is preferable that the ferrule 40 be detectable by a foreign object detecting device (e.g. a metal detector) so that if the cord should pull out of the earplug the cord can be detected.

The band can hold itself in place in different ways. One way is by radially (toward the earplug body axis) compressing the elastomeric material of the earplug body. Another way is by placing the band so it lies in a body groove, so it is difficult to slide the band axially off the body. The band is shown in FIGS. 1–4 uses both of these ways. it is also possible to provide a band that closely encircles the body and that does not compress the body or lie in a groove, but that is bonded to the body and is held by both bonding and encirclement; the encirclement is more than 180° about the body axis preferably over 270° (the gap is no more than 90°), and more preferably over 330° (the gap is no more than 30°).

Thus, the invention provides an earplug that can be readily detected if it falls into a batch of material. The earplug includes an earplug body and an attachment, referred to as a band, that extends around the body and that is clamped thereto. The earplug body has a maximum outside diameter of more than 0.38 inch to block even large ear canals, and the outside diameter of the band is less than 0.28 so it is less than the diameter of even small ear canals. Where the earplug body is of a type that has a stem and at least one flange extending generally rearwardly and radially outwardly from the stem, the band preferably extends around a location on the band which lies radially within the flange, and preferably within a groove formed in the stem. The band can have opposite ends that are initially separated to form a gap of at least 15°, and the earplug body width can be reduced at the location where the band will be mounted, so the location can be slipped through the gap and the gap then can be closed to clamp the band onto the stem.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A detectable earplug, comprising:
    an earplug body of a resilient polymer, with a front portion constructed to fit in a person's ear to block noise;
    detectable band means for detection, which extends by more than 180° around said earplug body and which is held to a location on said earplug body, to thereby enable detection of the earplug.

2. The earplug described in claim 1 wherein:
    said band means has a gap and is clamped to said body, to compress said body at said location.

3. The earplug described in claim 1 wherein:
    said band means extends at least 330° but less a continuous 360° around said body.

4. The earplug described in claim 1 wherein:
    said earplug body has an axis extending in forward and rearward directions, has a stem extending along said axis, and has at least one deflectable flange extending from said stem generally at a radially-outward rearward incline to said axis;
    said detectable band means extends around a location on said stem which lies radially within said flange.

5. The earplug described in claim 1 wherein:
    said earplug body has a groove at said location and said band means lies in said groove.

6. A detectable earplug comprising:
    an earplug body comprising a stem extending in forward and rearward directions along a body axis, and at least one flange joined to said stem at a predetermined position and extending around said flange and generally in a radially outward and rearward direction from said position, with said flange having a rear end and being deflectable;

a metal band extending around said stem at a location that is rearward of said position but forward of said flange rear end.

7. A method for use with an earplug body of elastomeric material, comprising:

placing a metal band around said earplug body so the band holds itself to the earplug body to form an earplug that can be detected.

8. A detectable earplug comprising:

an earplug body comprising a stem extending in forward and rearward directions along a body axis, and at least one flange joined to said stem at a predetermined position and extending around said flange and generally in a radially outward and rearward direction from said position, with said flange having a rear end;

a metal band extending around said stem at a location that is rearward of said position but forward of said flange rear end;

said stem has a recess at said location and has a greater diameter immediately rearward of said recess than in said recess, and said band lies in said recess.

9. A method for use with an earplug body of elastomeric material wherein the earplug body has a body axis and front and rear ends comprising:

placing a metal band that has band ends and a band axis, around said earplug body with said band axis extending substantially parallel to said body axis, so the band holds itself to the earplug body to form an earplug that can be detected;

said step of placing a metal band includes establishing said band with a gap of more than 15" between said band ends and deforming said earplug body along said axis to reduce the width of an earplug body location, while moving said band onto said body at said location;

compressing said band to reduce the width of said gap, to securely clamp said band onto said earplug body.

10. An earplug comprising:

an elastomeric polymer earplug body;

a metal band lying around said elastomeric earplug body and held thereto to form an earplug that can be detected.

* * * * *